United States Patent [19]

Schmidt

[11] Patent Number: Plant 5,377

[45] Date of Patent: Dec. 25, 1984

[54] ALMOND TREE (PEARL)

[76] Inventor: Robert H. Schmidt, 13500 Tim Bell Rd., Waterford, Calif. 95386

[21] Appl. No.: 515,859

[22] Filed: Jul. 21, 1983

[51] Int. Cl.[3] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is medium size, dense, vigorous, and precocious; foliated with medium size, acuminate, abruptly pointed, thin, smooth leaves having a coarsely serrate margin, long slender petiole, and small, green, alternate, globose glands; blooms heavily with white flowers; and is a regular and heavy bearer of nuts borne in clusters on short spurs; the out-of-hull nuts being of medium size and well sealed, and the out-of-shell kernels being of medium size, ovate, and plump.

1 Drawing Figure

BACKGROUND OF THE VARIETY

Field of the Invention

In the operation of my ranch located near Waterford, Stanislaus County, Calif., I am often present on such ranch in connection with usual agricultural activities such as cultivation and irrigation as well as for routine inspection. Against the background of these activities, the present variety of almond tree was discovered by me.

CLASSIFICATION OF THE VARIETY

The present new and distinct variety of almond tree is embraced by Class 30, Plants, of the U.S. Patent Office Manual Of Classification.

PRIOR VARIETIES

Among the existing varieties of nut and fruit trees which are known to me, and mentioned herein, are the peach tree Lovell (unpatented), and almond trees Nonpareil (unpatented), Mission (unpatented), Merced (U.S. Plant Pat. No. 1,730), Thompson (U.S. Plant Pat. No. 1,526), and Ruby (U.S. Plant Pat. No. 1,698).

ORIGIN OF THE VARIETY

The present variety of almond tree was discovered by me growing, as a chance seedling, on a roadside adjacent my aforesaid ranch. Under close and continuing observation of such chance seedling, I recognized that it bore certain new and distinct characteristics, and hence I determined to effect asexual reproduction of said seedling tree in anticipation of potential commercialization.

ASEXUAL REPRODUCTION OF THE VARIETY

The present variety of almond tree was asexually reproduced—on my behalf and by a commercial nursery—by June budding on Lovell rootstock, and—in maturity—such reproductions ran true to the original tree (chance seedling) in all respects.

SUMMARY OF THE VARIETY

The present variety of almond tree is, characteristically, medium size, dense, vigorous, and precocious; foliated with medium size, acuminate, abruptly pointed, thin, smooth leaves having a coarsely serrate margin, long slender petiole, and small, green, alternate, globose glands; blooms heavily with white flowers, and is a regular and heavy bearer of nuts borne in clusters on short spurs; the out-of-hull nuts being of medium size and well sealed, and the out-of-shell kernels being of medium size, ovate, and plump.

The present variety of almond tree is further characterized by early tree maturity, and heavy bearing of medium size nuts which yield a medium size kernel compatible in marketing with "California" almond varieties as defined by the California Almond Growers Exchange; the nuts having a medium to high percentage of kernel to nut, and being well sealed and hence relatively resistant to damage by worms.

The present variety of almond tree is still further characterized:

By blooming and being interfruitful with the Nonpareil, and harvesting with the Thompson, Merced, and Ruby.

By the production of heavy crops even under adverse weather conditions.

By particular adaptation as an interplant in older Nonpareil-Mission orchards.

BRIEF DESCRIPTION OF THE DRAWING

The drawing is an illustration, my photographic reproduction in color, of twigs with leaves and nuts; a detached nut in hull; out-of-hull nuts; and a separate kernel.

DESCRIPTION OF THE VARIETY

The botanical details of this new and distinct variety of almond tree—with color definitions (except those in common color terms) referenced to Maerz and Paul Dictionary of Color (First Edition)—are as follows:

TREE

Size: Medium.
Density: Dense.
Vigor: Medium.

TRUNK

Form: Stocky.
Texture: Shaggy.

BRANCHES

Form: Medium.
Texture: Medium.
Lenticels: Numerous. Medium size.

Branching habit: Upright.
Color:
*New wood.*—Gray, dull.
*Mature wood.*—Brown, dull.

FOLIAGE

Quantity: Medium.

LEAVES

Size; Medium.
*Average length.*—$2\frac{1}{2}''$.
*Average width.*—$1\frac{1}{4}''$.
Shape: Acuminate. Abruptly pointed.
Thickness: Thin.
Texture: Smooth.
Margin: Coarsely serrate.
Petiole: Long. Slender.
Glands: Average number — 2. Alternate, small, globose, green, positioned on petiole.
Stipules: Distal on petiole.
Color
*Top side.*—Medium green (23-L-9).
*Under side.*—Lighter green (22-K-8).

BLOOM

Amount of bloom: Heavy.
Color: White.
Blooming period: With Nonpareil.

CROP

Bearing: Regular bearer — even under adverse weather conditions.
Productivity: Heavy.
Distribution of nuts on tree: In clusters on short spurs.
Harvest period: With Thompson, Merced, and Ruby.
Tenacity: Hangs well on tree. Easy to harvest. Easy to hull.

HULL

Outer surface: Smooth.
Pits: Pitted.
Form: Regular.
Thickness: Thick.
Flesh: Tough.
Suture: Depressed.
Color: Light green (21-J-5) without silvery sheen, spotting, or blush.
Dehiscence: Opens freely.
Splitting: Along suture.

NUT

Size: Medium.
*Average length.*—$1\frac{1}{4}''$.
*Width range.*—$\frac{5}{8}''$ *to* $\frac{3}{4}''$.
*Thickness range.*—$\frac{1}{2}''$ to $\frac{5}{8}''$.
*Weight range.*—16 To 18 nuts per ounce.
Form:

*Length/width.*—Ovate.
*Width/thickness.*—Medium.
Shell: Soft. Thin. Ragged.
Outer shell: Crumbling. Largely missing. Adheres to hull.
Inner shell: Hard. Well sealed.
Color: Tan (13-I-7).
Pits: Large. Numerous. Deep. Bound.
Base: Ventrally oblique.
Stem scar: Large. Obtuse.
Apex: Acute. Sharp. Shouldered. Prolonged at tip.
Wing: Narrow. Thin. Tapered toward apex.
Inner surface: Dark Color.
Ventral streak: Light.
Percentage of kernel to nut:
*Range.*—60%–65%.

KERNEL

Size: Medium.
*Length range.*—$\frac{5}{8}''$ to $\frac{5}{8}''$.
*Width range.*—$\frac{1}{2}''$ to $\frac{5}{8}''$.
*Average thickness.*—$\frac{1}{2}''$.
*Weight range.*—32 to 38 per ounce.
Form:
*Length/width.*—Ovate.
*Width/thickness.*—Plump.
Base: Square.
Stem scar: Large. Obtuse.
Apex: Obtuse. Acuminate. Blunt. Tip recurved.
Texture: Smooth. Furrowed.
Pellicle: Thin.
Pubescence: Smooth. Veined.
Color: Hazel tan (13-J-9).
Number of doubles: Few.
Flavor: Sweet. Normal. Slightly bitter.
Quality: Good.

RESISTANCE TO INSECTS AND DISEASES

No exceptional or unusual susceptibilities nor resistance noted.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, characterized in particular by early tree maturity, heavy blooming and being interfruitful with the Nonpareil, harvesting with the Thompson, Merced, and Ruby, and by heavy bearing of medium-size, well-sealed nuts having medium-size, ovate, plump kernels, and a medium to high percentage of kernel to nut.

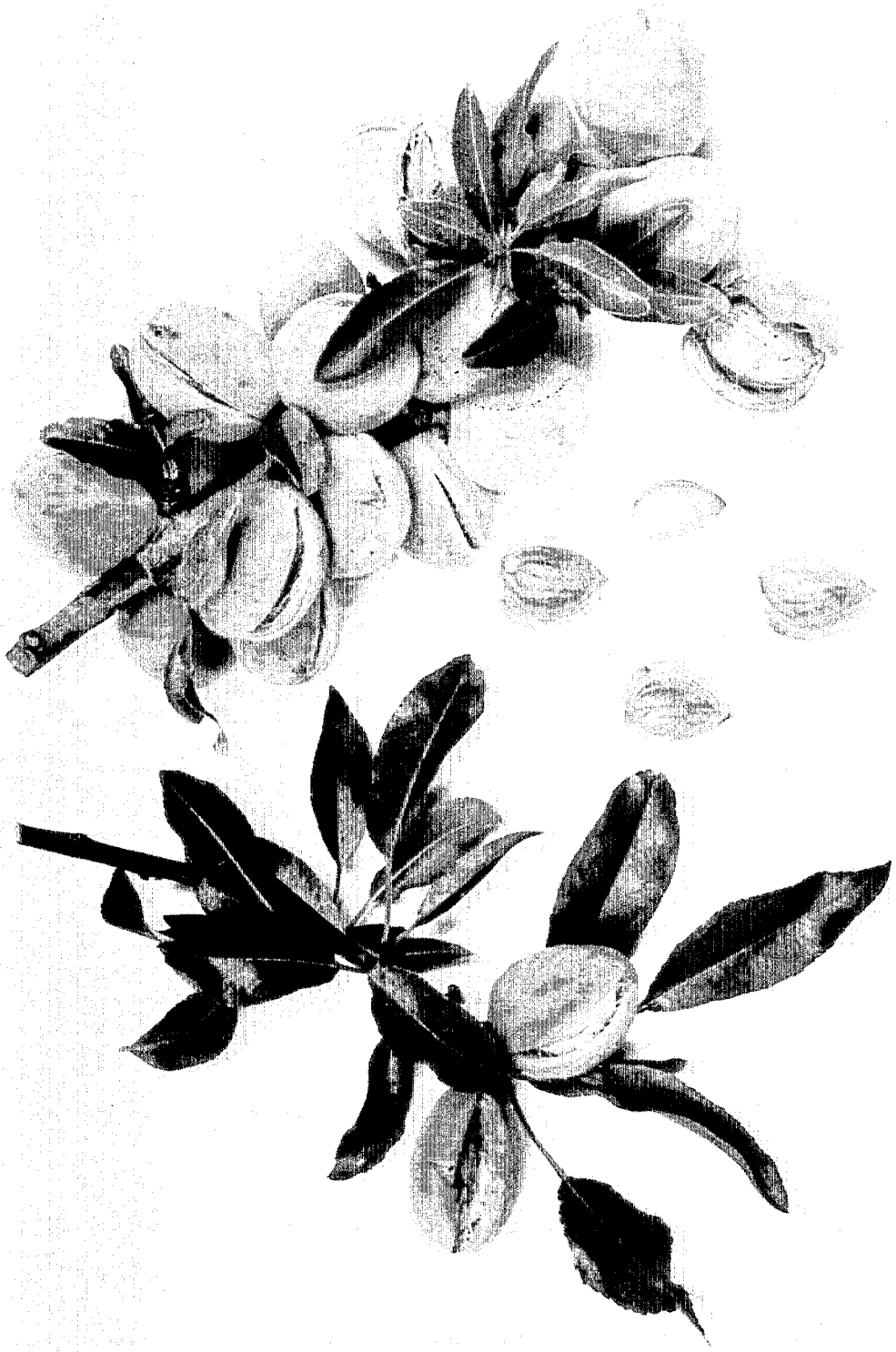

* * * * *